US007495300B2

(12) United States Patent
Gardner et al.

(10) Patent No.: US 7,495,300 B2
(45) Date of Patent: Feb. 24, 2009

(54) GAS-SENSING SEMICONDUCTOR DEVICES

(75) Inventors: Julian William Gardner, Warwickshire (GB); James Anthony Covington, West Midlands (GB); Florin Udrea, Cambridge (GB)

(73) Assignee: University of Warwick, Warwickshire (GB)

( * ) Notice: Subject to any disclaimer, the term of this patent is extended or adjusted under 35 U.S.C. 154(b) by 193 days.

(21) Appl. No.: 11/092,654

(22) Filed: Mar. 30, 2005

(65) Prior Publication Data
US 2006/0154401 A1 Jul. 13, 2006

(30) Foreign Application Priority Data
Jan. 10, 2005 (GB) ................... 0500393.4

(51) Int. Cl.
H01L 29/78 (2006.01)
(52) U.S. Cl. ............... 257/414; 257/252; 257/253; 257/401; 438/49; 436/151
(58) Field of Classification Search .............. 438/53, 438/49, 22, 48; 257/252, 253, 401, 414
See application file for complete search history.

(56) References Cited

U.S. PATENT DOCUMENTS

| | | | | |
|---|---|---|---|---|
| 4,413,502 A * | 11/1983 | Ohta et al. | ............ | 73/23.31 |
| 5,545,300 A * | 8/1996 | Yun et al. | ............ | 204/424 |
| 5,821,402 A * | 10/1998 | Okajima et al. | ............ | 73/23.2 |
| 5,827,438 A | 10/1998 | Blomberg et al. | | |
| 6,171,378 B1 * | 1/2001 | Manginell et al. | ............ | 96/143 |
| 6,248,609 B1 * | 6/2001 | Vigna et al. | ............ | 438/49 |
| 7,104,113 B2 * | 9/2006 | Zribi et al. | ............ | 73/31.05 |
| 7,157,054 B2 * | 1/2007 | Toyoda et al. | ............ | 422/88 |
| 2002/0142478 A1 * | 10/2002 | Wado et al. | ............ | 436/151 |
| 2003/0039586 A1 * | 2/2003 | Toyoda et al. | ............ | 422/98 |
| 2005/0050944 A1 * | 3/2005 | Ha et al. | ............ | 73/53.01 |
| 2005/0199041 A1 * | 9/2005 | Weber et al. | ............ | 73/31.06 |

FOREIGN PATENT DOCUMENTS

| | | |
|---|---|---|
| JP | 2002116171 | 4/2002 |
| JP | 2003294672 | 10/2003 |
| WO | WO 02/080620 A1 | 10/2002 |

* cited by examiner

*Primary Examiner*—W. David Coleman
*Assistant Examiner*—Su C Kim
(74) *Attorney, Agent, or Firm*—Squire, Sanders & Dempsey, LLP

(57) ABSTRACT

A gas-sensing semiconductor device is fabricated on a silicon substrate having a thin silicon oxide insulating layer in which a resistive heater made of a CMOS compatible high temperature metal is embedded. The high temperature metal is tungsten. The device includes at least one sensing area provided with a gas-sensitive layer separated from the heater by an insulating layer. As one of the final fabrication steps, the substrate is back-etched so as to form a thin membrane in the sensing area. Except for the back-etch and the gas-sensitive layer formation, that are carried out post-CMOS, all other layers, including the tungsten resistive heater, are made using a CMOS process employing tungsten metallisation. The device can be monolithically integrated with the drive, control and transducing circuitry using low cost CMOS processing. The heater, the insulating layer and other layers are made within the CMOS sequence and they do not require extra masks or processing.

34 Claims, 6 Drawing Sheets

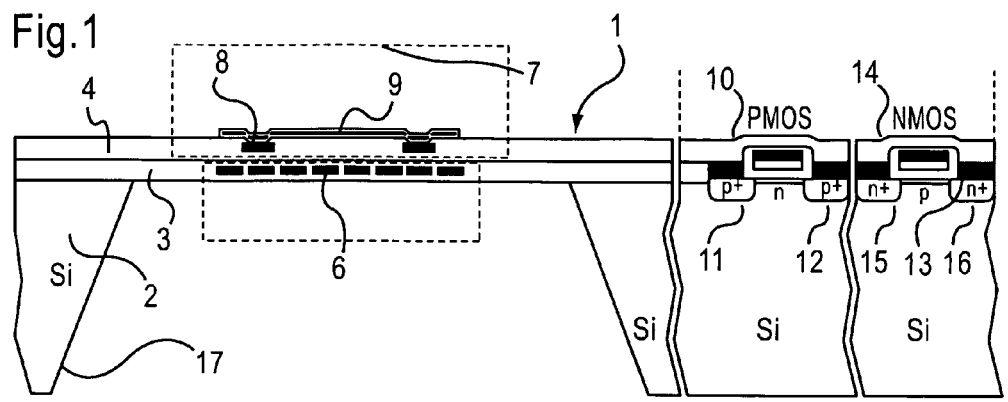
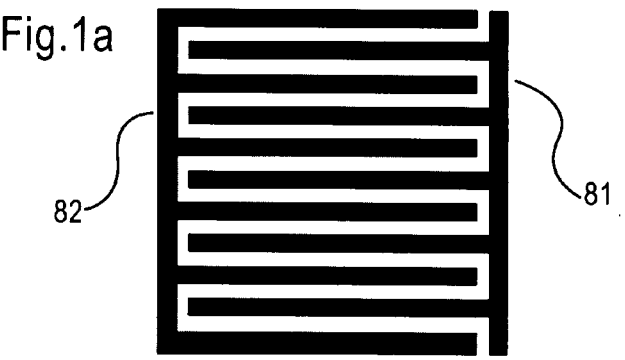
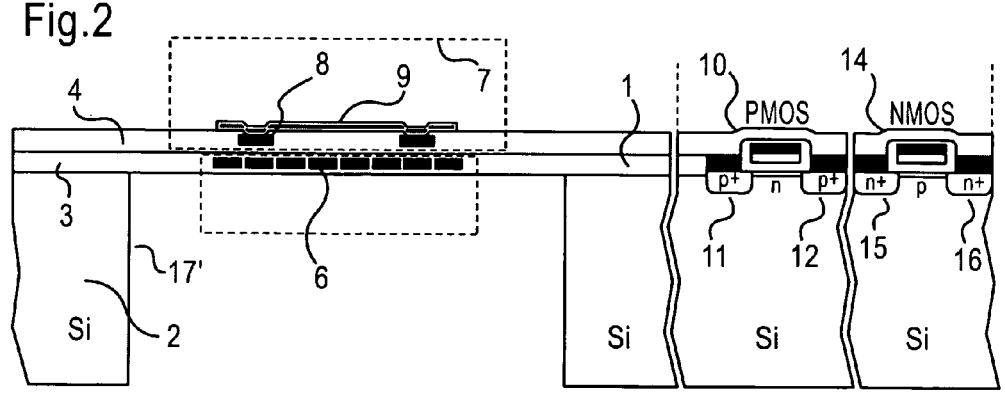

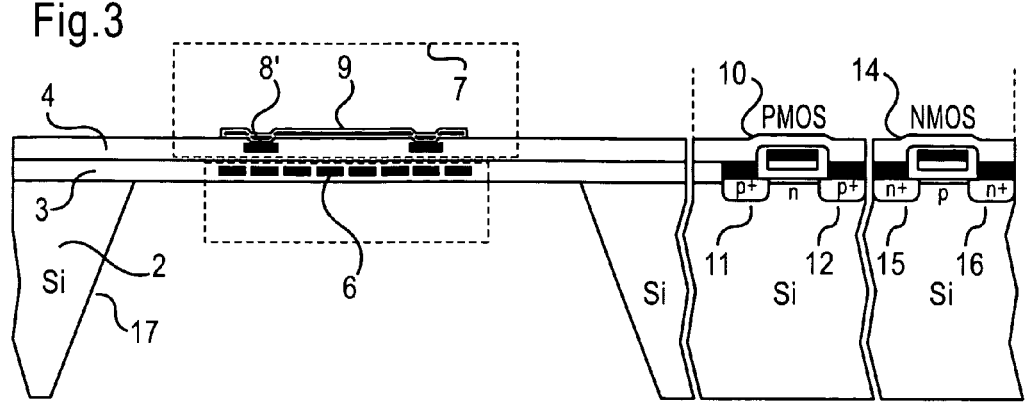
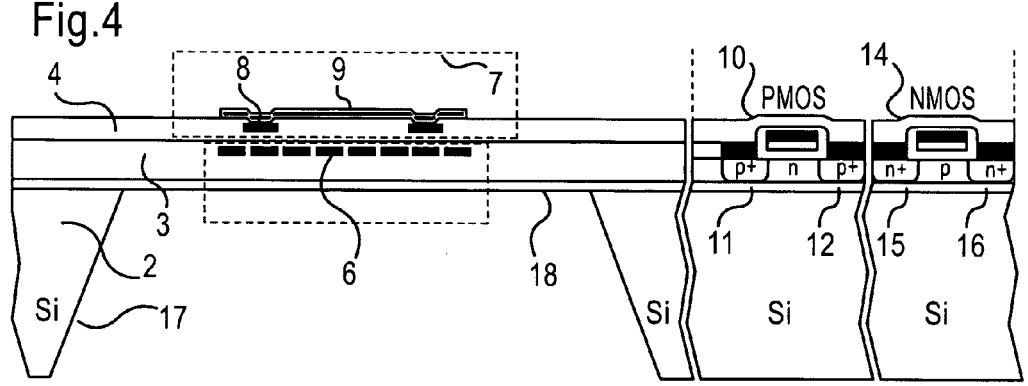
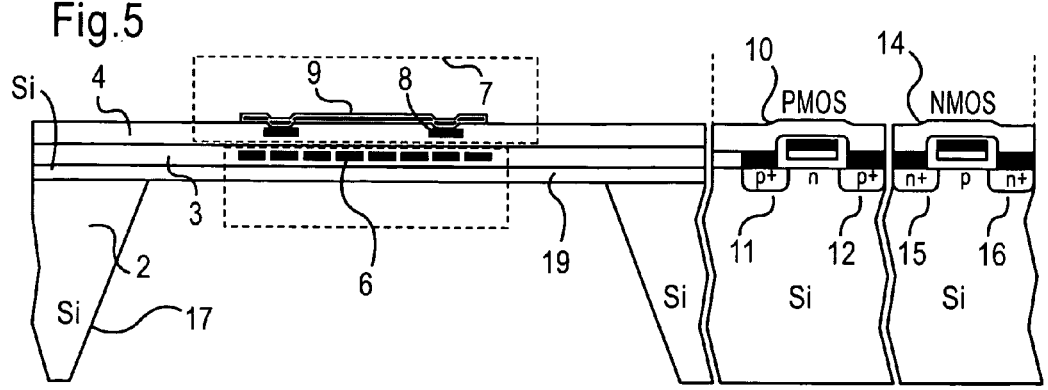

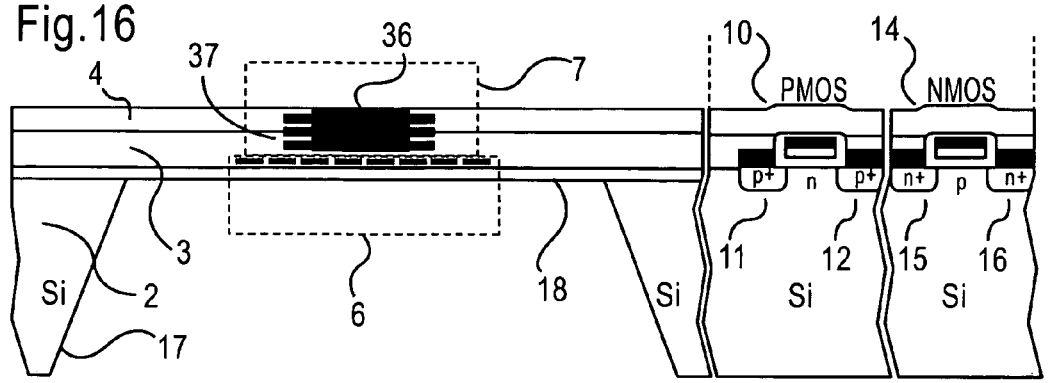
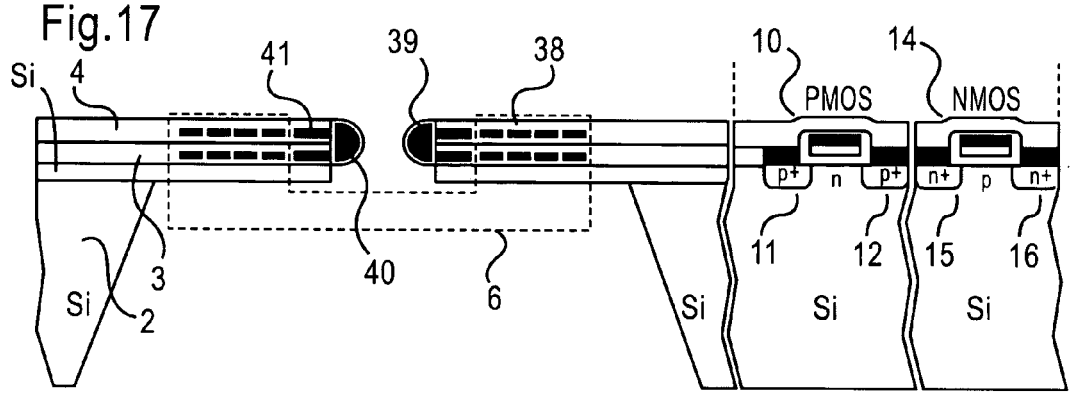
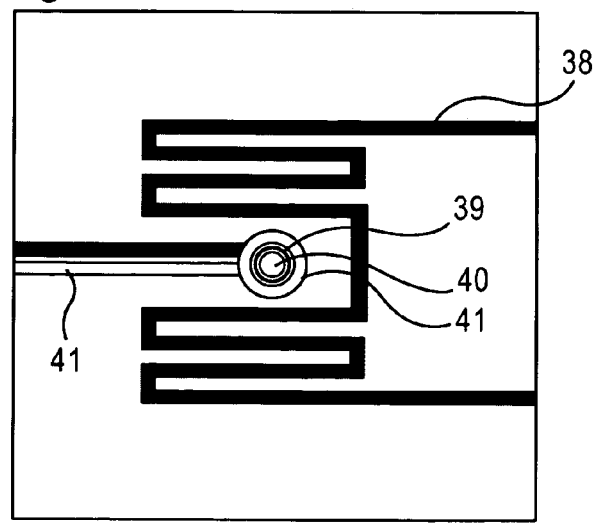

GAS-SENSING SEMICONDUCTOR DEVICES

BACKGROUND OF THE INVENTION

This invention relates to gas-sensing semiconductor devices for detecting the presence and/or concentration of one or more gases.

It is known to fabricate a gas microsensor within a semiconductor device. In particular it is known to produce high-temperature metal oxide conductimetric sensors using alumina substrates and semi-manual production methods. Recently attempts have been made to manufacture silicon versions of such sensors employing a platinum heater integrated with a thin insulating membrane of oxide or nitride. Such sensors offer lower power consumption than conventional sensors when operating at 300° C. to 600° C. However the two part deposition of the membrane of such a sensor and the deposition of the metal heater layer sandwiched between the two membrane layers makes the fabrication process incompatible with integrated circuit technology. There has also been much interest in the development of MOSFET potentiometric sensors using catalytic gates, for example of palladium which run at temperatures of between 120° C. and 200° C. However such sensors will have limited application due to their inefficiency and relatively high cost.

WO98/32009 discloses a gas sensor comprising a semiconductor substrate, a thin insulating layer on one side of the substrate, and a thin semiconductor layer on top of the thin insulating layer. The sensor includes at least one sensing area in which the material of the substrate has been removed to leave a membrane formed by the thin insulating layer and the thin semiconductor layer, the or each sensing area being provided with a gas-sensitive layer and a heater for heating the gas-sensitive layer to promote gas reaction with the gas-sensitive layer. Furthermore the or each sensing area incorporates a MOSFET formed in the thin semiconductor layer and forming part of the heater and/or sensor, and the sensor provides an electrical output indicative of gas reaction with the gas-sensitive layer. However such a gas sensor can only operate at relatively low temperatures because the parasitic bipolar transistor inherent in any MOSFET structure can turn on at high temperatures. In addition, if Aluminum is employed as in the CMOS metal layers, there is a maximum temperature of 250° C. beyond which long term degradation by electromigration or stress can occur.

There is a need to make small, low-cost gas sensing devices that incorporate a micro-heater to elevate the temperature of a gas-sensitive layer (e.g. tin oxide) and have integrated electronic circuitry. Gardner J. W., Pike A., de Rooij N. F., Koudelka-Hep M., Clerc P. A., Hierlemann A. and Gopel W., 1995 Sensors and Actuators, B 26 135-139, "Integrated chemical sensor array for detecting organic solvents" have reported the use of platinum or doped polysilicon to form a resistive track. However, platinum is a material that is not compatible with CMOS technology, and polysilicon requires additional process steps and forms heaters that tend to lack long-term stability. As referred to above, WO98/32009 discloses the use of a MOSFET to form an active heater but, in silicon technology, the operating temperature of the device is limited to about 300 to 350° C. (see Udrea F., Gardner J. W., Setiadi D., Covington J. A., Dogaru T., Lu C-C. and Milne W. I., 2001 Sensors and Actuators, B 78 180-190, "Design and simulations of a new class of SOI CMOS micro hot-plate gas sensors") and so is unsuited for, say, methane detection that requires an operating temperature of about 550° C.

The use of tungsten interconnects in high temperature CMOS processes is known. For example, in a paper by W. Yun, R. Howe, and P. Gray, "Surface micromachined, digitally force-balanced accelerometer with integrated CMOS detection circuitry," Proc. of the IEEE Solid-State Sensor and Actuator Workshop '92, p. 126, 1992, there is a description of the use of tungsten as metallisation in place of aluminium, in order to allow further post-CMOS high temperature processing, which tungsten can withstand successfully.

Tungsten has also been used as high temperature metallisation in SOI CMOS processes (see, for example, "Tungsten metallisation for high-temperature SOI devices", by J. Chen and J. P. Colinge, paper E-1.4, European Materials Research Society, Strasbourg, France, 1994, and Materials Science and Engineering).

However none of these references teaches the use of tungsten as a resistive heater in a CMOS compatible process.

It is an object of the invention to provide an improved high-temperature gas-sensing semiconductor device which can be produced at low cost using conventional bulk fabrication processes.

SUMMARY OF THE INVENTION

According to the present invention there is provided a gas-sensing semiconductor device comprising a semiconductor substrate, at least one sensing area provided with a gas-sensitive layer and a heater for heating the gas-sensitive layer to promote gas reaction with the gas-sensitive layer, and a sensor for providing an electrical output indicative of gas reaction with the gas-sensitive layer, wherein the heater has in its composition at least one layer of tungsten.

As compared with conventional planar integrated gas sensors, the use of a tungsten heater in a CMOS compatible process considerably simplifies the fabrication of the device, and thus decreases the manufacturing cost. Furthermore the device may be a resistive gas sensor or a calorimetric gas sensor and may be integrated with processing circuitry, such as a processor unit and a driving circuit, on a single chip so as to produce a "smart" gas microsensor. Unlike in conventional gas microsensors, the heater can be produced without requiring any fabrication steps in addition to those already employed in the IC processing. The use of one or more tungsten resistive heaters allows operation of the device at temperatures of well over 600° C., whilst permitting CMOS operation at over 200° C. (with a maximum of 250° C. for SOI) and allowing the heaters to be made relatively small.

SOI technology is commonly based on wafer bonding or implantation of oxygen deep into the substrate followed by epitaxial growth (known as SIMOX techniques). Other techniques such as smart-cut are also employed. CMOS SOI integrated circuits are fabricated by forming various transistors into the top semiconductor layer which is isolated from the substrate through a buried silicon oxide. Other insulating materials can be used in place of silicon oxide, such as silicon nitride or a combination of silicon oxide and silicon nitride. Individual semiconductor devices, such as MOSFET's, are then fabricated within the thin silicon layer using known fabrication steps. Because the electronic devices are formed within a very thin active semiconductor layer, of 0.5 to 1 µm thickness for example, SOI technology results in high speed/low power CMOS performance, as well as providing simple and efficient device isolation, reduced parasitic capacitances, latch-up elimination and reduced short-channel effects. In addition fully depleted devices (with an ultra-thin SOI layer) have been reported to have attractive features. They do not exhibit kink phenomena, have a sharp sub-threshold slope, and are stable in terms of dynamic floating body effects relating to impact-ionisation and charge-pumping phenomena. The SOI transistors also possess a lower off-state leakage current by a factor of about 10-100 when compared with conventional bulk silicon devices. This is important in reducing the stand-by power dissipation. In addition SOI technology enables device operation at higher temperatures than conventional devices, mainly due to reduced leakage currents.

Manufacturing CMOS compatible membranes with tungsten heaters allows very high temperatures in the membrane area (up to 600° C. or more for some sensing materials to react with the gases) and relatively high temperatures in the neighbouring circuit area (up to 250° C.) without being affected by high leakage currents or latch-up as in the case of conventional bulk CMOS processes. Therefore SOI technology is very well suited for smart gas sensors. Nevertheless, bulk CMOS with tungsten metallisation can also be employed as a slightly cheaper alternative.

In the gas-sensing semiconductor device of the invention the sensing area is preferably on a membrane formed by at least one thin insulating layer and a metal layer for making a resistive heater. The membrane is preferably formed by removing the substrate material, for example using an isotropic deep reactive ion back-etching process. In the case of bulk CMOS, the dielectric layer can be a standard CMOS interdielectric layer or a field oxide. In the case of CMOS SOI, the thin insulating layer is the silicon oxide buried layer which is part of the standard SOI structure. This layer serves a dual purpose, namely (i) it acts as an etch stop in the sensing area and thermally isolates the sensing area so as to reduce power losses at high temperatures, and (ii) it provides high grade electrical isolation from any associated integrated circuit area, incorporating transducer and associated processing circuitry for example, as well as providing reduced interferences, latch-up elimination and reduced capacitances in the specific case of low power CMOS SOI integrated circuits.

Due to the high thermal isolation properties of the membrane, high temperatures can be developed with very low electrical power consumption, and this is particularly advantageous in applications in which high temperatures are required for the gas to react with the active material of the gas-sensitive layer. The nature and concentration of different gases or of a mixture of gases can be determined by measuring the change in conductance of the gas-sensitive layer at different temperatures. Organic and catalytic-metal gas-sensitive layers may react at low temperatures (less than 100° C.) or medium temperatures (100° C. to 200° C.) whereas metal oxide gas-sensitive layers may require temperatures in excess of 200° C., and catalytic oxides may require temperatures in excess of 500° C. Thus a gas microsensor array device can be built by integrating several individual sensor cells utilising different gas-sensitive layers in the same chip. The individual sensor cells can be built on the same membrane or can have separate membranes. Such a microsensor array device possesses the advantages over individual sensors of improved gas selectivity, lower noise and reduced effect of poisoning through superior structural design or signal processing.

BRIEF DESCRIPTION OF THE DRAWINGS

In order that the invention may be more fully understood, a number of embodiments of the invention will now be described, by way of example, with reference to the accompanying drawings, in which:

FIGS. 1 to 5 show sections through a sensing area of different embodiments of the invention utilising a single layer resistive heater, FIG. 1*a* showing a plan view of sensor electrodes;

FIGS. 15 to 17 show sections through a sensing area of further different embodiments of the invention, FIG. 18 showing a plan view of the embodiment of FIG. 17.

DETAILED DESCRIPTION OF THE DRAWINGS

Figure 6:
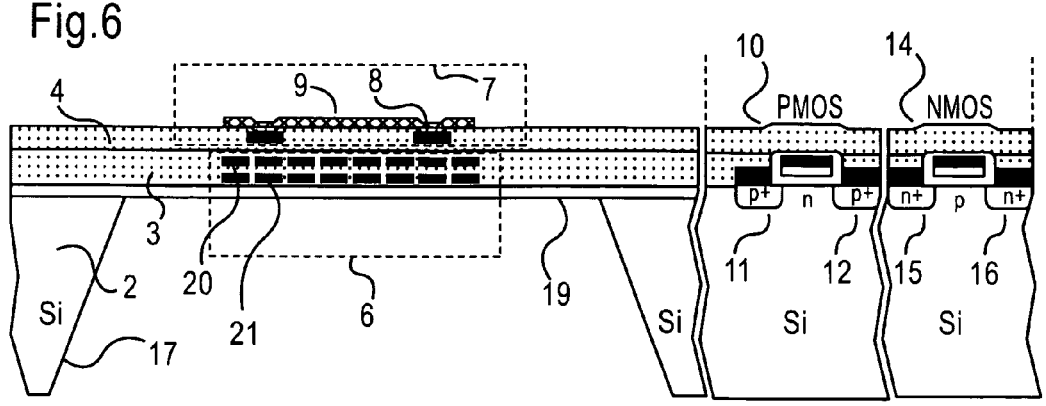
FIGS. 6, 7, 8 and 11 show sections through a sensing area of different embodiments of the invention utilising a two layer resistive heater, FIGS. 9 and 10 showing plan views of two alternative heater designs.

The embodiments of gas-sensing semiconductor device in accordance with the invention to be described with reference to the drawings are fabricated utilising non-SOI (e.g. standard bilk) or SOI (e.g. Smart Cut UNIBOND) CMOStechnologies so as to provide gas sensing areas integrated with IC circuitry in a single chip, each sensing area being a thin membrane formed by at least one thin insulating layer and a tungsten metal layer acting as a resistive heater. The structures in these embodiments can operate at temperatures well over 600° C. in the sensing area. The thin insulating layer, which provides thermal isolation, may be an oxide, a nitride, a combination of oxide and nitride or some other insulating material. Unlike in conventional gas microsensors, there is no need for low-stress special layer deposition involving an expensive and difficult fabrication process. Particular attention is drawn in the accompanying description to the fabrication of the device in the sensing areas, although it will be understood that IC fabrication will be effected simultaneously to provide the associated circuitry in other areas of the device.

In the embodiment of FIG. 1 the device 1 is fabricated on a silicon substrate 2 having a thin $SiO_2$ layer 3 on one side in a sensing area, and a thin insulating layer 4 on top of the $SiO_2$ layer 3. The thermal oxide has a much lower thermal conductivity than the silicon and therefore the thermal power losses in the sensing area will be greatly reduced. A resistive heater 6 made of tungsten is formed in the sensing area. This heater is formed within the CMOS process as part of the standard CMOS metallisation (and not as part of a post CMOS process). Thus the heater 6 in the sensing area and the source and drain metallisation 13 in the electronic area can be formed from the same tungsten layer which is been patterned by photolithography to define the individual metal structures. In addition to the heater 6, a chemoresistor sensor 7 is fabricated in the sensing area by placing a gas-sensitive layer 9 made either of an inorganic material (such as tin oxide) or an organic material (such as a polymer or pthalocyanine) so as to span two electrodes 8. The gas-sensitive layer 9 can be deposited by sputtering etc. or can be electrochemically grown onto the two electrodes 8 (as in the case of conducting polymers). The two electrodes 8 can be formed from a second tungsten metal layer using one of the upper metals formed as part of the CMOS metallisation, or can be of a different material such as gold and be deposited post-CMOS. Alternatively the electrodes 8 can be formed from a combination of several layers, partly within CMOS sequency and partly by post-CMOS processing. As one of the final steps in the fabrication process the substrate 2 is back-etched so as to form the thin membrane in the sensing area, with the $SiO_2$ layer 3 serving to stop the back-etching. The back-etching can be effected either by wet etching (e.g. KOH etrching) or by dry etching (e.g. deep reactive ion etching).

In the electronic area, the devices are formed using the known CMOS processing. There are several CMOS or Bi-CMOS processes available, using n-tub, p-tub, twin-tub or SOI technologies. The isolation, the geometry and composition of some layers and the order of the processing steps are different from one process to another but they all incorporate major common implantation and drive-in steps, formation of gate oxides, poly (one or two layer) deposition, and formation of one or several layers of metal to contact the transistor terminals and form the interconnects within the IC. Referring to FIG. 1 a silicon oxide layer is grown at the surface to form the gate oxide of an NMOS transistor 14 and a PMOS transistor 10 followed by the deposition and patterning of a polysilicon layer on top of the gate oxide. The p+ source 11 and p+ drain 12 are further implanted and could be self-aligned to the gate. An NMOS transistor 14 may be formed in broadly similar manner with the n+ source 15 and n+ drain 16 being implanted and self-aligned to the gate. Whichever type of transistor is produced a tungsten metalisation layer 13 is applied and patterned on top of the source and drain diffusions. This layer 13 is also used to produce a resistive heater 6 in the membrane area. Other tungsten metal layers can be subsequently formed for interconnect purposes and isolated from each other through interdielectric layers, commonly made of silicon oxide. A final passivation layer, made of silicon-oxide, nitride, oxynitride, glass or organic material is formed on top of the integrated circuit, covering the whole of the IC, except the pads which contain at least a top metal layer and preferably a stack of metal layers.

When current or voltage is supplied to the heater 6, the sensing area heats up rapidly due to the high thermal insulation in the sensing area and very low thermal capacitances, thus allowing gas molecules to react with the gas-sensitive layer 9 of the sensor 7. The heater 6 can be operated in open loop control applying a constant voltage or constant current. However, by monitoring the heater resistance, it is possible to modify the heater current or voltage in a closed loop control system. This permits very accurate setting of the heater temperature and hence the temperature of the gas-sensitive layer 9. When the gas interacts with the gas-sensitive layer 9, the conductivity of the gas-sensitive layer 9 changes, and this can be detected by appropriate detection circuitry (not shown). The temperature can be monitored by detecting the change in the heater resistance with respect to a reference at room temperature. A pair of electrodes 8 in the form of interdigitated electrodes 81 and 82, as shown in plan view in FIG. 1a, underlying the gas-sensitive layer 9 is used to measure the conductance or resistance of the gas-sensitive layer 9, and the electrical resistance of the gas-sensitive layer 9 is related to the concentration of the gas being analysed. Each of the individual fingers of the interdigitated electrodes 81 and 82 has a width in the range of 1-100 microns with the interfinger gap typically being in the range of 1-10 microns. In this case the aspect ratio if approximately the product of the finger length and the number of finger pairs divided by the gap width.

In order to monitor the temperature in the sensing area, a CMOS or Bi-CMOS integrated temperature sensor (not shown) can be fabricated in the sensing area adjacent to the gas-sensitive layer 9. Such a temperature sensor may be a passive sensor made of metal, polysilicon or silicon resistors or an active sensor made of unipolar or bipolar devices formed within the CMOS processing and may make use of variation of resistivity, the carrier mobility or the emitter-base voltage with temperature. Such temperature sensors are widely used and give accurate results.

The heater 6 may have a meandering structure to uniformly heat the sensing area. If the sensor comprises an array of individual sensor cells, a single common heater may be used for all the sensor cells, or alternatively an array of heaters may be employed. If required, such a heater array could be adapted to heat different sensor cells to different temperatures.

The use of tungsten interconnects in a CMOS process permits various design options. Some possible gas sensor designs are described below with reference to the drawings, the designs being listed according to the number of tungsten layers used. The minimum number would be a lateral heater made of tungsten next to a lateral resistive gas sensor. Instead of a resistive gas sensor, a calorimetric gas sensor may be provided with a similar structure except that the heater or a temperature sensor is used to measure the rise or fall in temperature of the gas-sensitive layer. In some cases it may be necessary to provide a metal plate on which the gas-sensitive material may be deposited electrochemically. However this is not normally necessary as the gas-sensitive layer may be deposited by sputtering, electroless plating, physical or chemical vapour deposition, etc.

The tungsten heater would have to be larger than a corresponding design of heater made from platinum because of the higher electrical conductivity of tungsten. In certain applications it may therefore be desirable for the heater to comprise a number of vertical heating layers.

Heater Designs with One Tungsten Layer

The first design option is to provide a single layer resistive heater made of tungsten (within the CMOS metallisation sequence) in combination with one or more lateral resistive gas sensors. FIGS. 1, 2 and 3 show three variations, namely the embodiment already described above with reference to FIG. 1 utilizing an anisotropic back etch so as to produce tapered side walls 17 (using for example wet etching of the 100 silicon substrate), an alternative embodiment as shown in FIG. 2 utilizing an anisotropic back etch so as to produce parallel side walls 17' (using dry etching such as deep reactive ion etching for example), and an alternative embodiment as shown in FIG. 3 uses an alternative to tungsten, preferably gold, for the sensing electrodes 8'.

A second design option is based on a SOI CMOS or Bi-CMOS process. In this design a resistive heater made of tungsten is used in combination with one or more lateral resistive gas sensors and lateral oxide isolation. In the embodiment of FIG. 4 a buried oxide layer 18, specific to SOI technology, is used to isolate the transistors from the substrate in the electronic area. This buried oxide layer 18 can also be used as a back-etch stop. The active silicon above the buried oxide layer 18 has been removed in the sensing area (by etching or oxidation) and in its place there is layer of silicon oxide that provides efficient thermal isolation.

A third design option is to provide a resistive heater made of tungsten in combination with an electrochemical etch stop and one or more lateral resistive gas sensors. In the embodiment of FIG. 5 a thin silicon layer 19, which is part of the original substrate 2, is left un-etched to provide a temperature spreading plate. This helps to make the temperature more uniform in the sensing area but results in greater power losses. The thin silicon layer 19 is doped and forms a rectifying junction with the substrate silicon. The current flowing across the junction will change when the junction is etched way.

Heater Designs with Two Tungsten Layers

The first design option in this case is to provide a two layer resistive heater made of tungsten with one or more lateral resistive gas sensors, such an arrangement comprising two tungsten heating layers 20 and 21, as shown in FIG. 6, in effect constituting two micro-heaters arranged one above the other and serving to increase the heat input by a factor of two for the same area as compared with a corresponding design employing only a single heating layer.

Figure 7:
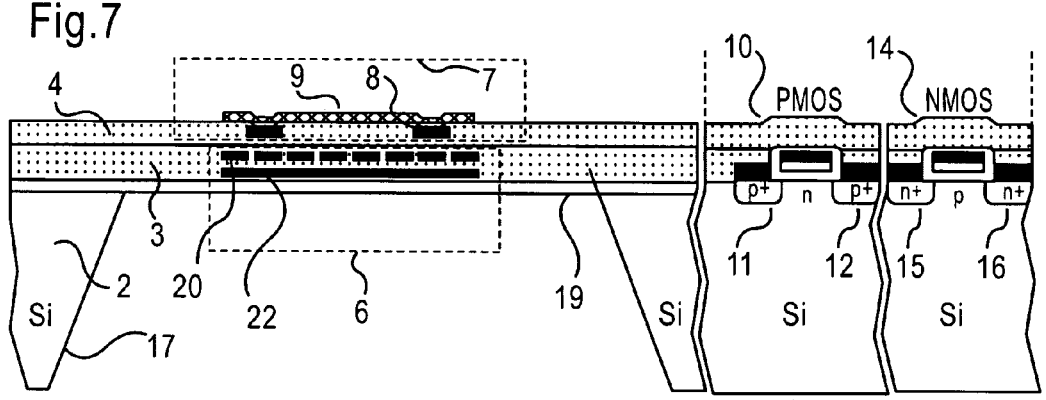

A second design option is to provide a resistive heater in the form of a first tungsten layer with a spreading plate in the form of a second tungsten layer and lateral resistive gas sensors, such an arrangement comprising a tungsten heating layer 20 and a tungsten spreading plate 22 arranged one above the other, as shown in FIG. 7, and serving to increase the heat input by a factor of two for the same area as compared with a corresponding design employing only a single heating layer. The spreading plate 22 serves to spread the heat generated by the heating layer 20 and to direct it towards the gas-sensitive layer 9.

Figure 8:
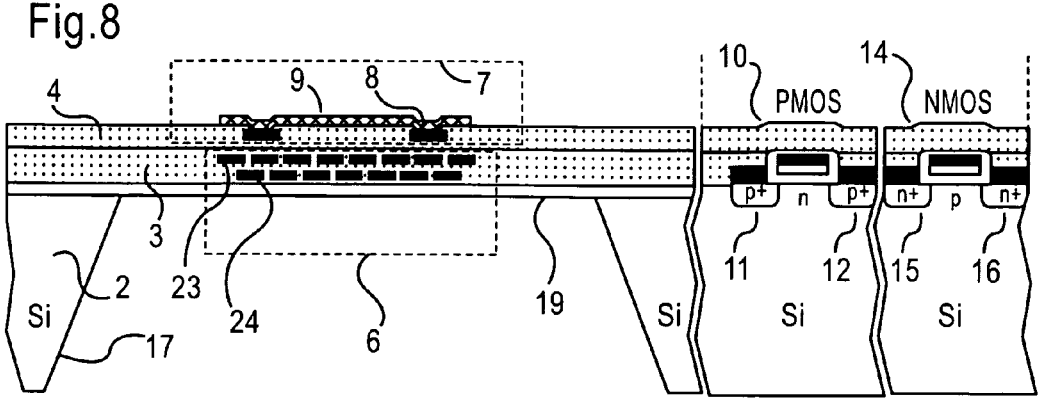
Figure 9:
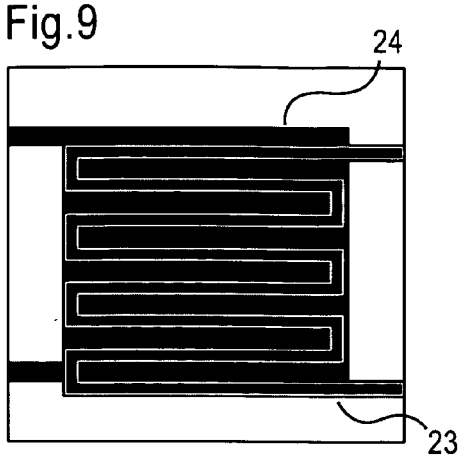
Figure 10:
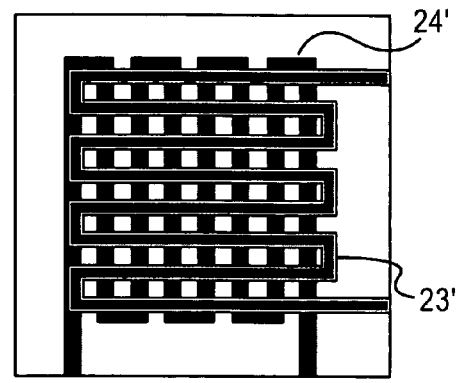

A third design option is to provide a two layer resistive heater with one or more lateral resistive gas sensors, such an arrangement comprising two tungsten heating layers 23 and 24 arranged one above the other and interlaced with one another, as shown in FIG. 8, in effect constituting two micro-heaters arranged one above the other and serving to increase the heat input by a factor of two for the same area as compared with a corresponding design employing only a single heating layer. The interlacing creates a more isothermal surface profile. FIG. 9 shows a plan view of one possible design in which the heating layers 23 and 24 follow meandering paths that are offset laterally relative to one another, whereas FIG. 10 shows a plan view of another possible design in which the heating layers 23' and 24' follow meandering paths that are orthogonal to one another.

Figure 11:
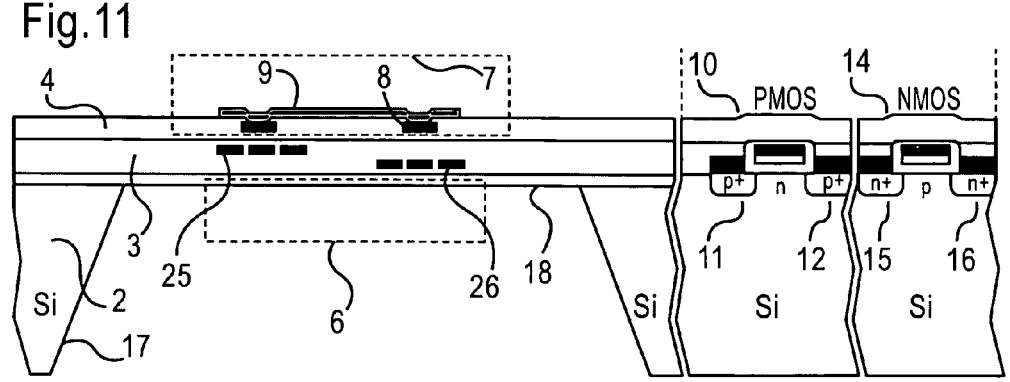

A fourth design option is to provide a two layer resistive heater with one or more lateral resistive gas sensors, such an arrangement comprising two tungsten heating layers 25 and 26 laterally offset relative to one another, as shown in FIG. 11, to create a temperature gradient relative to the gas sensor electrodes 8. Such an arrangement could be used for ratiometric measurements for a sensing material at two different (steady-state) temperatures.

A fifth design option is to provide a two layer resistive heater with one or more lateral resistive gas sensors, such an arrangement (which is not illustrated) comprising two tungsten heating layers arranged one above the other and connected in series to increase the electrical resistance of the heater and thus limit the driving current. The two heating layers may be interconnected by via connections between the layers that may be placed outside the area of the membrane produced by the back etching in order to increase the reliability of lateral resistive gas sensors.

Heater Designs with More Than Two Tungsten Layers

Figure 12:
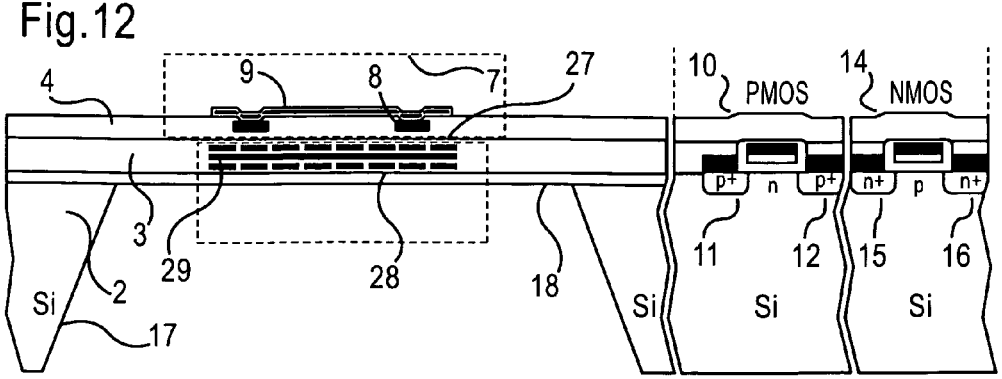
FIGS. 12 to 14 show sections through a sensing area of different embodiments of the invention utilising a multi-layer resistive heater.

The first design option in this case is to provide a two layer resistive heater comprising two tungsten heating layers 27 and 28 arranged one above the other and an intermediate tungsten spreading plate 29, as shown in FIG. 12, with one or more lateral resistive gas sensors. One or more of the layers can be used as heat sinking plates to make the temperature more uniform across the heater area by conducting the heat laterally. For example the tungsten standard heater (Metal 2) can be placed below a square heat sink (Metal 1/3) to create a more isothermal surface.

Figure 13:
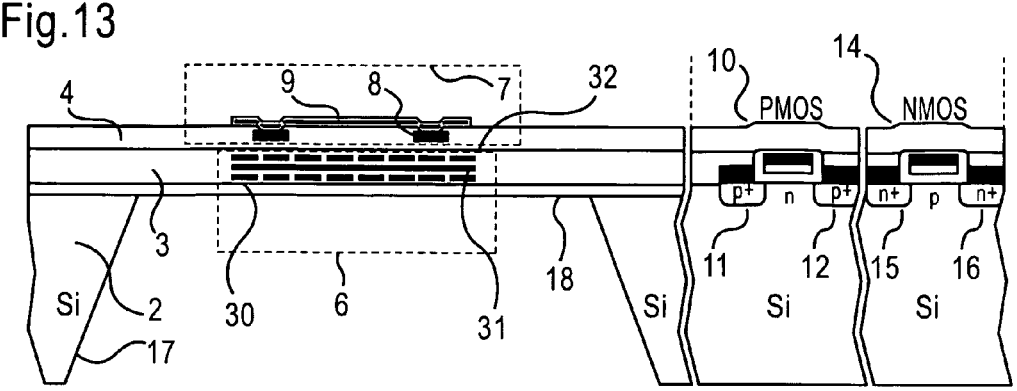

A second design option is to provide a single layer resistive heater comprising a single tungsten heating layer 30, a tungsten spreading plate 31 and a temperature sensor 32, as shown in FIG. 13, with one or more lateral resistive gas sensors. The temperature sensor 32 is made of tungsten, its role being not to heat the structure but only to measure the change in its resistance at high temperatures. The power generated by the sensor 32 is negligible compared to the power generated by the actual heating layer 30.

Figure 14:
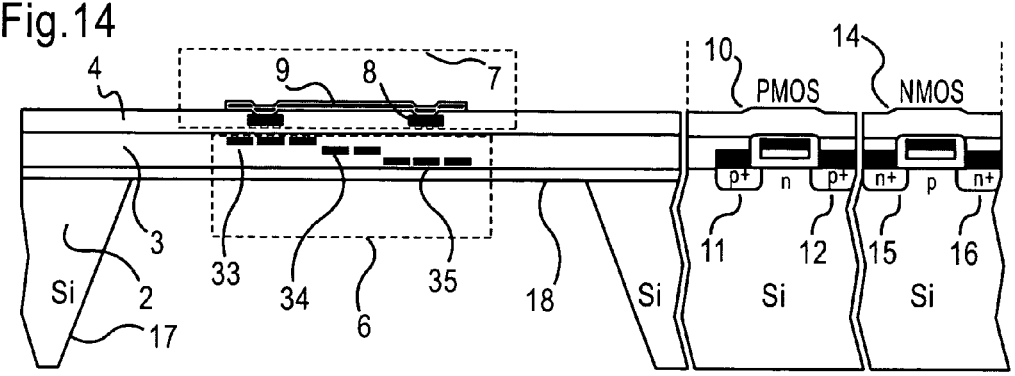

A third design option is to provide a triple layer resistive heater comprising three tungsten heating layers 33, 34 and 35 laterally offset relative to one another, as shown in FIG. 14, with one or more lateral resistive gas sensors. Such an arrangement reduces the area needed and allows three different operating temperatures to be switched in digitally.

Employing more than one heater within the same membrane can be advantageous in some cases. For example, one of the heaters may be used to set a temperature DC bias and another heater may be used to modulate the heat. The modulation can be effected by applying a low frequency AC signal.

Heater Designs with Tungsten Layers and Vertical Sensing Structures

Figure 15:
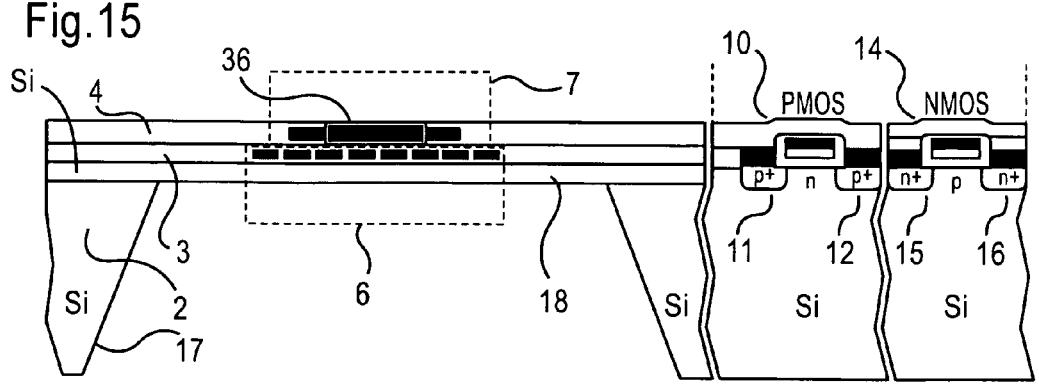

FIG. 15 shows a single layer resistive heater provided with one or more vertical resistive gas sensors 36, that is with one or more sensing electrodes stacked on top of one another rather than beside one another (lateral configuration). In this configuration the gas-sensitive layer is below the surface of the device, allowing the area of the sensor to be reduced. The sensor can be made more compact without compromising its sensitivity. If two resistive sensing electrodes are configured on the same side of a trench, then the gap between two sensing electrodes can be below 1 micron. If the two resistive sensing electrodes are used across the trench, then the gap between two sensing electrodes depends upon the trench width.

FIG. 16 shows a single layer resistive heater with multiple vertical electrodes 37 for multiple resistive gas sensors 36. This arrangement enables a set of fast measurements to be taken as the gas diffuses in to the trench for spatio-temporal measurements.

FIG. 17 shows one or more layers of a resistive lateral heater 38 surrounding vertically spaced electrodes 41 surrounding an air gap 40 and a vertical resistive gas sensor 39. This arrangement can be used for flow sensors and other types of device. FIG. 18 is a plan view of the device showing a circular air gap (it could alternatively be square, etc.) and two resistive heating layers superimposed on one another (not separately visible in this view).

The provision of multi-layers in this manner allows new designs of resistive heater to be provided that can be driven in different ways. One such design of heater could be used to provide heating up to a base temperature (say 100° C.) and to be capable of being switched to provide increased heating up to a measurement temperature (say 300° C.). Such a heater could be switched digitally and would therefore require only a very simple control circuit. Furthermore lateral two heater structures could be provided to from temperature gradients across the gas sensor, but such structures would take up more area and would therefore be less efficient than vertical structures.

The following improvements over existing gas sensors may be provided by embodiments of the invention:

1) Operation well over 600° C. Polysilicon cannot provide such high temperatures because of long-term stability. It is also difficult to set the precise characteristics of the doped layer. Active FET heaters cannot be used above 350° C., and so tungsten heaters are particularly useful as microcalorimeters to detect hydrogen and methane.

2) Better mechanical strength and Young's modulus as compared with devices using Si, Al or Pt (see Table 1).

3) Standard CMOS processes use several aluminium layers to interconnect silicon devices in a chip. However aluminium is unsuitable for high-temperature heaters because of its low melting point.

4) The metal layer of the heater must satisfy certain conditions to render it suitable for a wide range of applications. In particular it must have:

a) An electrical conductivity that is high enough to permit high-speed CMOS operation and reduce any parasitic resistive interconnect paths.
b) An electrical conductivity that is sufficiently low to make the heater small enough to be a low power and low unit cost. The heater resistance needs to be reasonably high to allow lower current drive with CMOS voltage operation (maximum 5V).
c) The heater material must have a high melting point so that it can be operated at up to 900° C.
5) In addition the heater design must produce an isothermal structure. All these conditions are met through the use of tungsten metal layers in a high-temperature CMOS process.

The electrical conductivity of tungsten is lower than aluminium and gold which helps in the design of smaller resistive heaters, although it is not as low as platinum. However platinum is not a CMOS compatible material. Tungsten has much higher yield strength than the other materials and so should be more robust.

6) As opposed to aluminium, tungsten does not suffer from electromigration. This means it can take more power and higher current density than aluminium without risk of reliability failure. This also means that the tungsten metal tracks can be made thinner, resulting in a more compact heater.
7) The tungsten heater can also be used as a temperature sensor. Its TCR (temperature coefficient of resistance) is 50% higher than platinum, which means it has a 50% higher sensitivity as a temperature sensor. Alternatively, a separate temperature sensor made of tungsten can be used.
8) Tungsten is used as a high temperature interconnect metal in SOI (Bi)CMOS processes. This allows an IC to operate at temperatures up to 250° C. Therefore the temperature in the electronic area of the sensor can be well in excess of that of an IC chip with aluminium metallisation. It is therefore possible to use such sensors in very high temperature environments.

For the reasons stated above it will be appreciated that tungsten is a particularly advantageous material for a resistive heater for use in a high-temperature micro-hotplate gas sensing device. The following Table 1 illustrates the desirable properties of W as compared with the corresponding properties of Al, Au and Pt.

TABLE 1

Properties of some metals

| Property | Al | W | Au | Pt |
|---|---|---|---|---|
| Electrical conductivity, $\sigma$ ($10^3$ S/cm) | 377 | 183 | 488 | 94 |
| Melting point, $T_{mp}$ (° C.) | 660 | 3,410 | 1,064 | 1,772 |
| Density, $\rho_m$ (kg/m$^3$) | 2,702 | 19,350 | 19,320 | 21,450 |
| Temperature coefficient of resistance, $\alpha_r$ ($10^{-4}$/K) | 39 | 45 | 34 | 30 |
| Work function, f (eV) | 4.3 | 4.6 | 5.1 | 5.6 |
| Thermal conductivity, $\kappa$ (W/m/K)[1] | 236 | 177 | 319 | 72 |
| Specific heat capacity, $c_p$ (J/K/kg) | 904 | 134 | 129 | 133 |
| Linear expansivity, $\alpha_l$ ($10^{-6}$ K$^{-1}$) | 23.1 | 4.5 | 14.2 | 8.8 |
| Young's modulus, $E_m$ (GPa) | 70 | 411 | 78 | 168 |
| Yield strength[2], Y (MPa) | 50 | 750 | 200 | <14 |
| Poisson's ratio, $\nu$ | 0.35 | 0.28 | 0.44 | 0.38 |

The above structures can also be used as microcalorimeters (or as both chemoresistors and microcalorimeters) in which the additional heat liberated or absorbed by the gas-sensitive layer in the presence of the gas is detected. In this case the temperature of the sensing material changes as a result of its reaction with the gas so that the nature of the gas and/or its concentration can be determined by monitoring the heat liberated or absorbed by the gas-sensitive layer in the presence of the gas. An appropriate gas-sensitive layer for such an application would be a non-electrically conducting material such as Γ-alumina (pellistor). Chemoresistive materials such as tin oxide change their thermal conductivity so that it is possible to monitor the change in thermal conductivity, the heat liberated and the change in the electrical conductivity at high temperatures.

We claim:

1. A smart sensor comprising a gas-sensing device monolithically integrated with an electronic circuit incorporating control elements for drive, control and transducing functions, wherein the sensor has been fabricated using CMOS, Bi-CMOS or SOI based technology and including a fabrication step in which a layer of tungsten is applied to form simultaneously both (i) a metallization layer for contacts and interconnects between the control elements in the electronic circuit and (ii) a heater of the gas-sensing device.

2. The smart sensor according to claim 1, comprising a semiconductor substrate, wherein the gas-sensing device has at least one sensing area provided with a gas-sensitive layer to be heated by the heater to promote gas reaction with the gas-sensitive layer, and sensing means for providing an electrical output indicative of gas reaction with the gas-sensitive layer.

3. The smart sensor according to claim 1, wherein the sensing means incorporates laterally spaced electrodes in the vicinity of the gas-sensitive layer.

4. The smart sensor according to claim 2, wherein the gas-sensitive layer is provided around the periphery of an air gap extending through a membrane.

5. The smart sensor according to claim 2, wherein the gas-sensitive layer is of tin oxide.

6. The smart sensor according to claim 2, wherein said at least one sensing area incorporates temperature sensing means.

7. The smart sensor according to claim 2, wherein the material of the substrate has been removed in at least one sensing area to leave a membrane incorporating the sensing area.

8. The smart sensor according to claim 2, wherein the material of the substrate has been removed in at least one sensing area by back etching.

9. The smart sensor according to claim 2, wherein said at least sensing area is integrated with at least one electronic circuit area incorporating associated circuitry.

10. The smart sensor according to claim 2, wherein an insulating layer is provided on one side of the substrate.

11. The smart sensor according to claim 10, wherein the heater is embedded in the insulating layer.

12. The smart sensor according to claim 10, wherein the insulating layer is a silicon oxide layer.

13. The smart sensor according to claim 10, wherein a passivation layer is provided on the insulating layer on one side of the substrate.

14. The smart sensor according to claim 13, wherein a conductive polymer layer is provided which acts as the gas-sensitive layer.

15. The smart sensor according to claim 13, wherein the gas-sensitive layer is formed on the passivation layer.

16. The smart sensor according to claim 1, wherein the heater is a meander-shaped tungsten heater.

17. A smart sensor according to claim 1, comprising a semiconductor substrate, at least one sensing area provided with a gas-sensitive layer and a heater for heating the gas-sensitive layer to promote gas reaction with the gas-sensitive layer, and a sensor for providing an electrical output indicative of gas reaction with the gas-sensitive layer, wherein the heater has in the heater's composition at least one layer of tungsten and comprises two or more heating layers powered.

18. The device according to claim 17, wherein the heating layers are offset laterally relative to one another.

19. The device according to claim 17, wherein the heating layers are interlaced relative to one another.

20. The smart sensor according to claim 1, wherein the heater incorporates a spreading plate.

21. The smart sensor according to claim 1, which has been produced utilising CMOS, Bi-CMOS or SOI CMOS processing steps, or Bi-CMOS processing steps followed by a post-CMOS back-etch.

22. The smart sensor according to claim 1, which is a resistive gas-sensing device.

23. The smart sensor according to claim 1, which is a calorimetric gas-sensing device.

24. The smart sensor according to claim 1, wherein the material of the substrate has been removed in at least one area to leave a membrane.

25. The smart sensor according to claim 24, wherein the removal of the material of the substrate to define the membrane has been carried out by deep reactive ion etching.

26. The smart sensor according to claim 24, wherein the removal of the material of the substrate has been carried out by anisotropic wet etching.

27. A gas-sensing semiconductor device comprising a semiconductor substrate, at least one sensing area provided with a gas-sensitive layer and a heater for heating the gas-sensitive layer to promote gas reaction with the gas-sensitive layer, and a sensor for providing an electrical output indicative of gas reaction with the gas-sensitive layer, wherein the heater has in the heater's composition at least one layer of tungsten, and wherein the sensor incorporates laterally spaced tungsten electrodes in the vicinity of the gas-sensitive layer.

28. The device according to claim 27, wherein the gas-sensitive layer is located between the electrodes.

29. The device according to claim 27, wherein the electrodes incorporate two or more electrodes spaced vertically one above the other.

30. A method of fabricating a smart sensor, comprising a gas-sensing device monolithically integrated with an electronic circuit incorporating control elements for drive, control and transducing functions using CMOS, Bi-CMOS or SOI-based technology, wherein the method includes applying a layer of tungsten to form simultaneously both (i) a metallization layer for contacts and interconnects between the control elements in the electronic circuit and (ii) a heater of the gas-sensing device.

31. A method according to claim 8, wherein the gas-sensing device has at least one sensing area provided with a gas-sensitive layer to be heated by the heater to promote gas reaction with the gas-sensitive layer, and a sensing unit for providing an electrical output indicative of gas reaction with the gas-sensitive layer.

32. A method according to claim 30, which includes removing the material of the substrate in at least one area in a post-CMOS process to leave a membrane.

33. A method according to claim 32, wherein the removal of the material of the substrate is carried out by deep reactive ion etching.

34. A method according to claim 32, wherein the removal of the material of the substrate is carried out by anisotropic wet etching.

* * * * *